United States Patent
Dulal et al.

(10) Patent No.: US 12,232,714 B2
(45) Date of Patent: Feb. 25, 2025

(54) PUPIL EXPANDER ASSEMBLY

(71) Applicant: Ambler Surgical, LLC, Exton, PA (US)

(72) Inventors: Rohit Dulal, Boston, MA (US); Anand S, Pune (IN); Vrushket Barge, Pune (IN); Martin Anthony, Exton, PA (US); Balarama Krishna Reddy Keesari, Pune (IN)

(73) Assignee: Ambler Surgical, LLC., Exton, PA (US)

( * ) Notice: Subject to any disclaimer, the term of this patent is extended or adjusted under 35 U.S.C. 154(b) by 0 days.

(21) Appl. No.: 18/662,212

(22) Filed: May 13, 2024

(65) Prior Publication Data

US 2024/0382187 A1    Nov. 21, 2024

Related U.S. Application Data

(60) Provisional application No. 63/466,413, filed on May 15, 2023.

(51) Int. Cl.
*A61B 17/02* (2006.01)
*A61F 9/007* (2006.01)

(52) U.S. Cl.
CPC ...... *A61B 17/0231* (2013.01); *A61B 17/0293* (2013.01); *A61F 9/00736* (2013.01)

(58) Field of Classification Search
CPC . A61B 17/0231; A61B 8/4209; A61B 8/4236; A61F 9/00736
See application file for complete search history.

(56) References Cited

U.S. PATENT DOCUMENTS 5,267,553 A * 12/1993 Graether ............... A61F 9/007
                                                    623/4.1
5,427,088 A *  6/1995 Graether ............... A61F 2/15
                                                    606/107

(Continued)

FOREIGN PATENT DOCUMENTS

CN      215651310      1/2022
WO     WO202161551    12/2021

OTHER PUBLICATIONS https://www.beye.com/product/i-ring-pupil-expander. retrieved Jan. 12, 2023.

*Primary Examiner* — Eduardo C Robert
*Assistant Examiner* — Steven J Cotroneo
(74) *Attorney, Agent, or Firm* — Joseph E. Maenner; Petock & Petock LLC (57) ABSTRACT

A pupil expander assembly includes a delivery device having a body having a proximal end portion, a distal end portion, and a longitudinal axis. A discharge port extends distally from the distal end portion. An expander receiver is located inside the body in the distal end portion and has a proximal slot and a distal slot, each of which extends along the longitudinal axis. The proximal slot and the distal slot are both in fluid communication with the discharge port. A slider is slidingly disposed in the body and configured to longitudinally translate along the longitudinal axis. A hook extends distally from the slider and is configured to slide through the proximal slot and the distal slot and out the discharge port. A pupil expander is disposed in the expander receiver and configured to be pushed distally by the hook through the distal slot and the discharge port for delivery.

18 Claims, 11 Drawing Sheets

(56) References Cited

U.S. PATENT DOCUMENTS

| | | | |
|---|---|---|---|
| 6,280,449 B1* | 8/2001 | Blake | A61F 2/1664 606/107 |
| 6,620,098 B1 | 9/2003 | Milverton | |
| 7,422,604 B2* | 9/2008 | Vaquero | A61F 2/1691 623/6.12 |
| 7,879,090 B2* | 2/2011 | Pynson | A61F 2/1678 606/107 |
| 8,439,833 B2 | 5/2013 | Christensen et al. | |
| 8,496,583 B1* | 7/2013 | Reynard | A61B 17/0231 600/235 |
| 8,852,091 B2 | 10/2014 | Sussman et al. | |
| 10,716,555 B2 | 7/2020 | Girard et al. | |
| 11,147,544 B2* | 10/2021 | Dykes | A61F 9/0017 |
| 11,389,150 B2 | 7/2022 | Cote et al. | |
| 2002/0022881 A1* | 2/2002 | Figueroa | A61F 2/167 606/107 |
| 2003/0092970 A1* | 5/2003 | Lee | A61B 17/0231 600/236 |
| 2008/0269888 A1* | 10/2008 | Malyugin | A61B 17/0231 623/6.38 |
| 2013/0096386 A1* | 4/2013 | Christensen | A61B 17/0231 600/206 |
| 2013/0267988 A1* | 10/2013 | Sussman | A61B 17/0231 606/198 |
| 2014/0276900 A1* | 9/2014 | Cote | A61B 17/0231 606/107 |
| 2015/0366704 A1 | 12/2015 | Eippert | |
| 2017/0319062 A1* | 11/2017 | Charles | A61B 90/20 |
| 2018/0206835 A1 | 7/2018 | Canabrava | |
| 2022/0125422 A1 | 4/2022 | Malyugin et al. | |
| 2023/0200794 A1* | 6/2023 | Akura | A61B 17/0293 600/206 |
| 2023/0404563 A1* | 12/2023 | Mackool | A61F 9/007 |

* cited by examiner

PUPIL EXPANDER ASSEMBLY

CROSS-REFERENCE TO RELATED APPLICATION

The present application claims the benefit of U.S. Provisional Patent Application Ser. No. 63/466,413, filed on May 15, 2023, which is incorporated herein by reference in its entirety.

BACKGROUND OF THE INVENTION

Field of the Invention

The invention relates to a pupil expander and a delivery device to deliver the expander to a patient's eye and to retrieve the expander after use.

Description of the Related Art

Pupil expanders are known to engage the rim of an iris and push the rim back to enlarge the visible area of the underlying pupil so that an ophthalmologist can access a more peripheral area of the pupil for surgery.

It would be beneficial to provide a pupil expander that can be delivered and retracted by the same hook device with the ring being folded in on itself during delivery to the eye. It would also be beneficial to provide a pre-loaded pupil dilator with an expansion ring that has controlled inside-out circular expansion.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, the present invention is a pupil expander assembly that includes a delivery device having a body having a proximal end portion, a distal end portion, and a longitudinal axis. A discharge port extends distally from the distal end portion. An expander receiver is located inside the body in the distal end portion and has a proximal slot and a distal slot, each of which extends along the longitudinal axis. The proximal slot and the discharge slot are both in fluid communication with the discharge port. A slider is slidingly disposed in the body and configured to longitudinally translate along the longitudinal axis. A hook extends distally from the slider and is configured to slide through the proximal slot and the distal slot and out the discharge port. A pupil expander is disposed in the expander receiver and configured to be pushed distally by the hook through the distal slot and the discharge port for delivery.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION

In the drawings, like numerals indicate like elements throughout. Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

The word "about" is used herein to include a value of +/−10 percent of the numerical value modified by the word "about" and the word "generally" is used herein to mean "without regard to particulars or exceptions."

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

The present invention provides a pupil expander assembly for expanding an iris to increase accessibility to the underlying pupil. The assembly can be used by an ophthalmologist to provide better access to the periphery of the pupil during surgery. Additionally, the device provides a pupil expander that can be delivered and retracted by the same hook device with the ring being folded in on itself during delivery to the eye. The pupil expander ring also has controlled inside-out circular expansion for better control of the ring during the expansion phase of the use of the inventive assembly.

Figure 1:
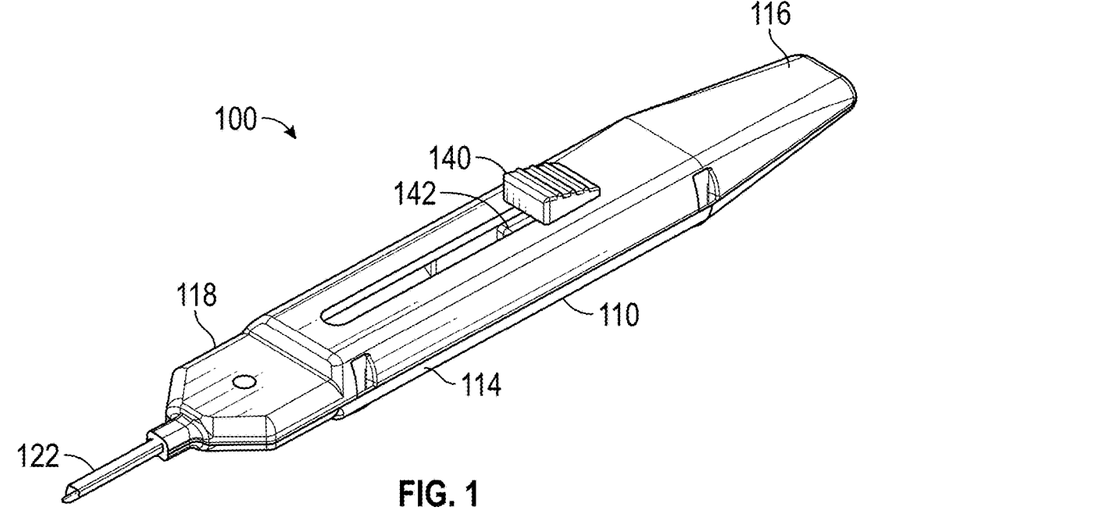
FIG. 1 is a perspective view of a pupil expander assembly according to an exemplary embodiment of the present invention.
Figure 2:
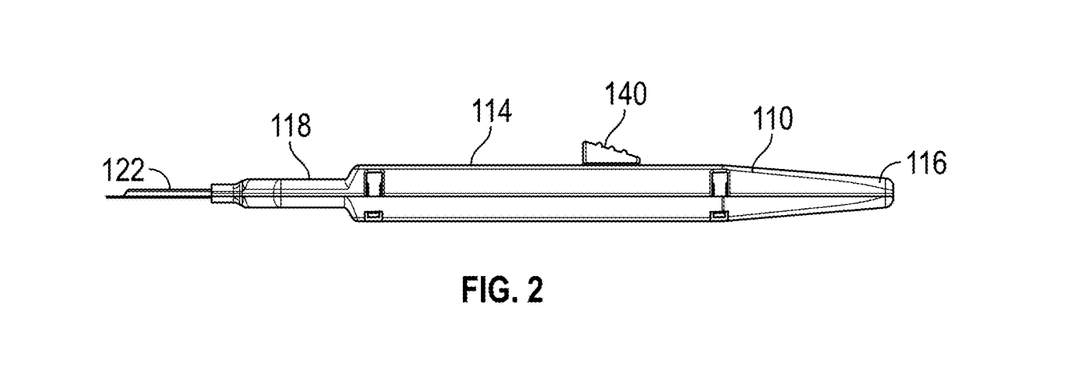
FIG. 2 is a side elevational view of the pupil expander assembly of FIG. 1.
Figure 3:
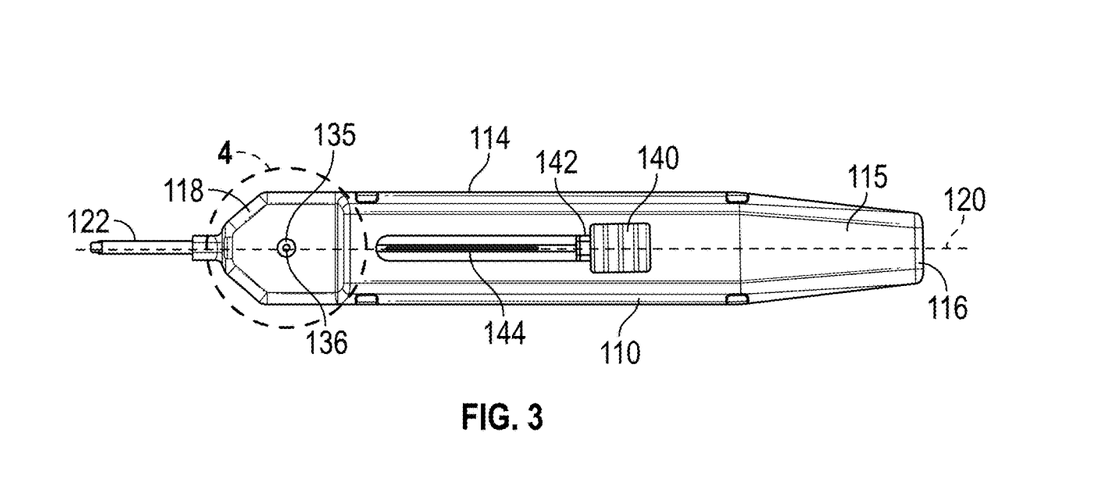
FIG. 3 is a top plan view of the pupil expander assembly of FIG. 1.

As shown in FIGS. 1-3, a pupil expander assembly 100 ("assembly 100") according to an exemplary embodiment of the present invention is shown. Assembly 100 includes a delivery device 110 with an expander ring 170 located inside the delivery device 110. Instead of expander ring 170 being packaged with delivery device 110, expander ring 170 can be provided in a tray or cartridge housing (not shown), and can be packaged separately from delivery device 110. Prior to use, the tray or cartridge housing is configured to be inserted into delivery device 110, facilitating deployment of expander ring 170 into an eye 50.

Delivery device 110 includes an elongated body 114 having top surface 115, a proximal end portion 116, a distal end portion 118, and a central longitudinal axis 120 extending between the proximal end portion 116 and the distal end portion 118. Body 114 can be constructed from a rigid material, such as a polymer and is ergonomically sized and shaped for use by a single hand of a clinician. Such a construction allows for the other hand of the clinician to remain free.

Figure 4:
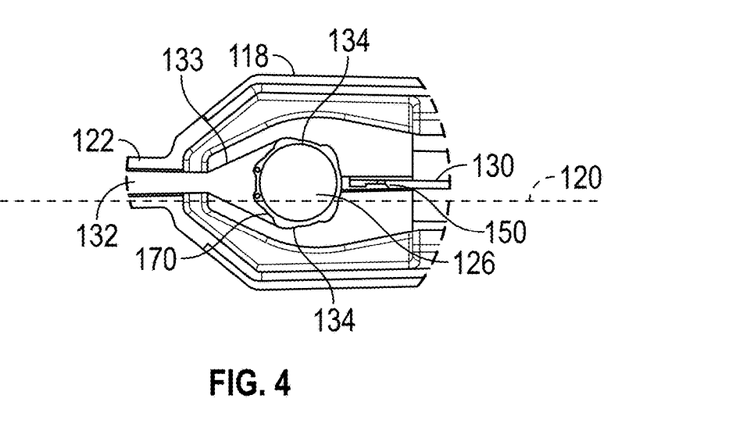
FIG. 4 is an enlarged view, with the top cover removed, of area 4 of FIG. 3.
Figure 5:
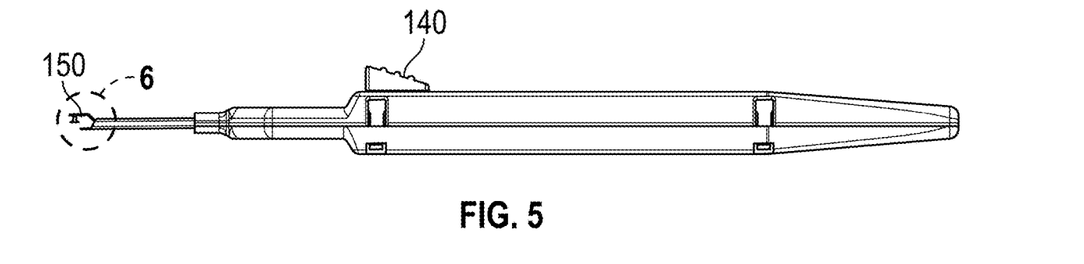
FIG. 5 is a side elevational view of the pupil expander assembly of FIG. 1, with a hook extended distally.
Figure 6:
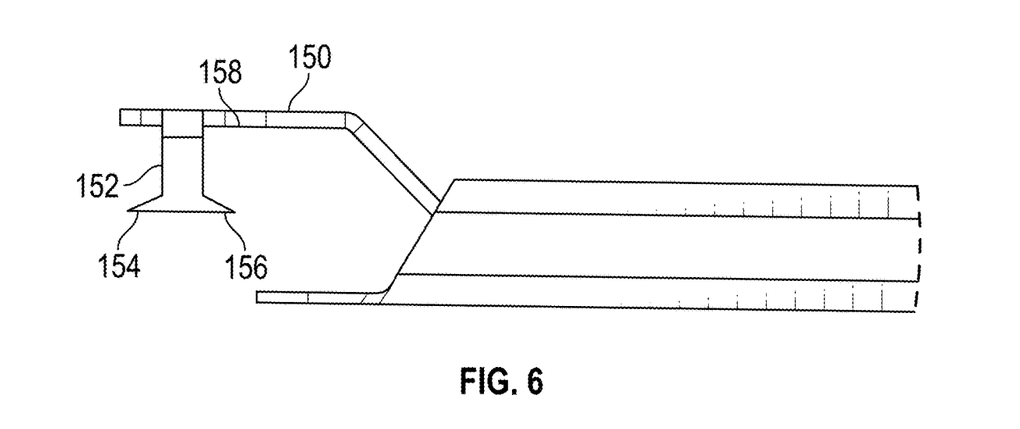
FIG. 6 is an enlarged view of area 6 of FIG. 5.
Figure 7:
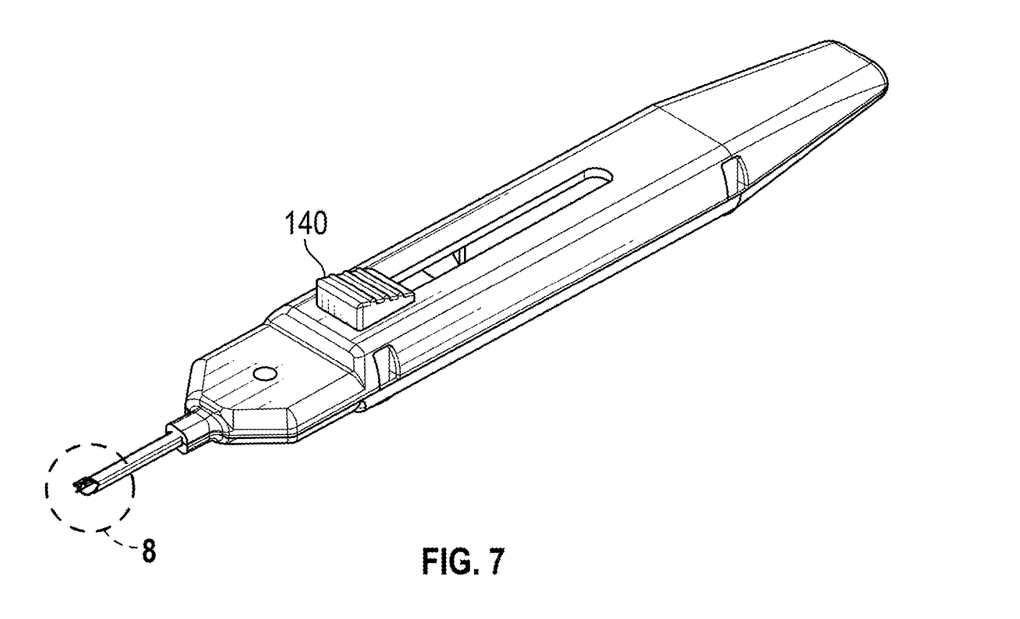
FIG. 7 is a perspective view of the pupil expander assembly of FIG. 5.
Figure 8:
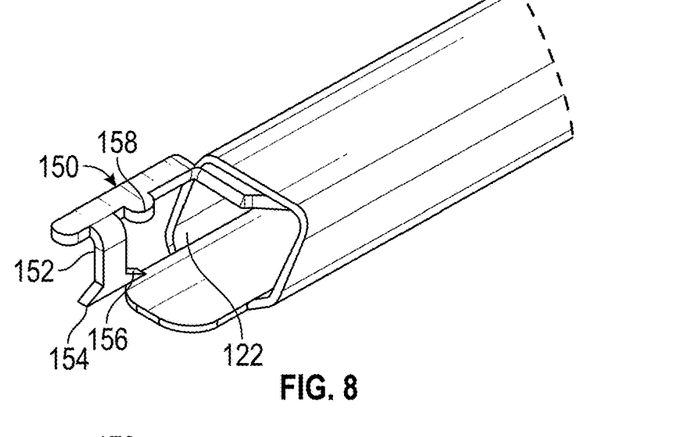
FIG. 8 is an enlarged view of area 8 of FIG. 7.

Referring to FIG. 4, a discharge port 122 extends distally from the distal end portion 118 of body 114. While discharge port 122 can be an opaque metal, such as aluminum or surgical stainless steel, those skilled in the art will recognize that discharge port 122 can be constructed from a transparent material so that the user can see the movement of expander ring 170 through discharge port 122.

Expander ring 170 can be loaded into and discharged from delivery device via discharge port 122, as will be explained in further detail below. An expander receiver 126 is located inside the body 114 in the distal end portion 118. The expander receiver 126 has a proximal slot 130 and a distal slot 132. Both of the proximal slot 130 and the distal slot 132 extend along the central longitudinal axis 120 such that the proximal slot 130 and the discharge slot 132 are both in fluid communication with the discharge port 122.

The expander receiver 126 tapers from wider to narrower in a proximal to distal direction, forming a teardrop shape with the apex toward the distal end portion of the expander receiver 126. Further, a wall 133 defining the expander receiver 126 comprises a plurality of detents 134 extending into the expander receiver 126. The detents 134 serve to seat and align the expander ring 170 in the expander receiver 126 for delivery through the discharge port 122.

Referring to FIG. 3, a viewing port 135 is provided disposed above the expander receiver 126 in top surface 115 of body to allow a clinician to better view the expander ring 170 inside the expander receiver 126 and confirm that the expander ring 126 is properly seated in the expander receiver 126 to allow for proper discharge of the expander ring 170 from the delivery device 110. Optionally, magnifying lens 136 can be provided in the viewing port to enlarge the view of the expander ring 170.

Figure 3A:
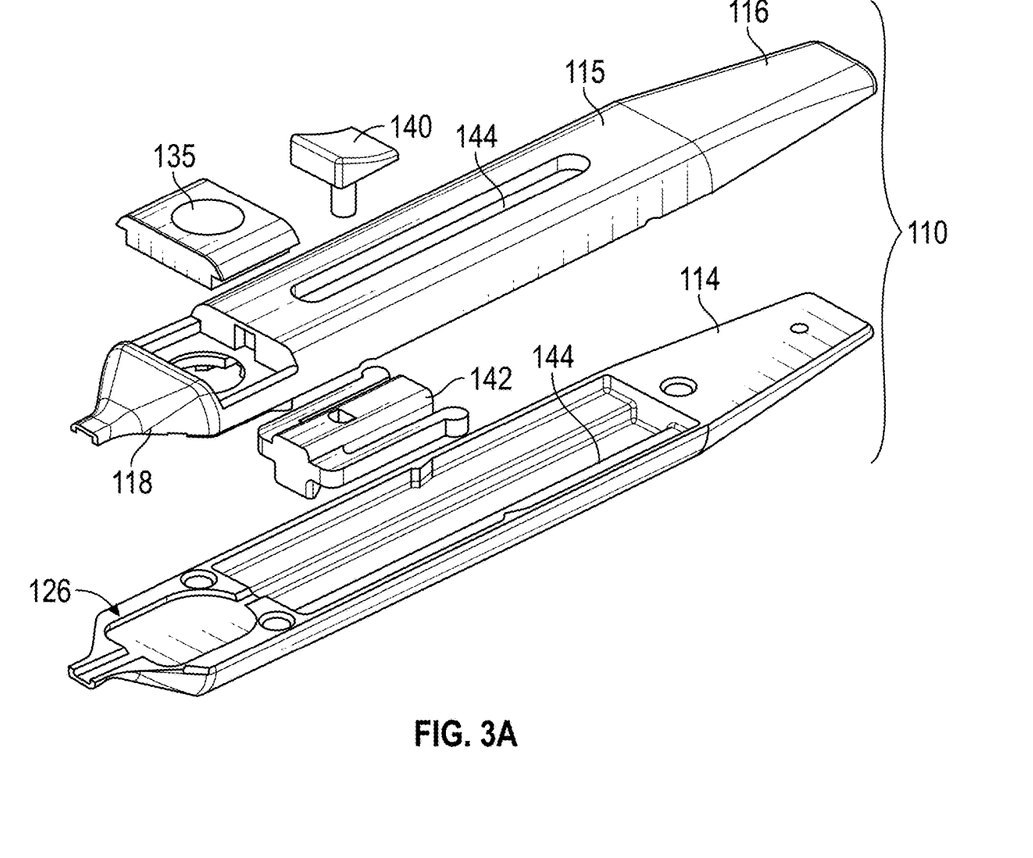
FIG. 3A is an exploded view of the pupil expander assembly of FIG. 1.

Referring back to FIGS. 1-3, a slider 140 is slidingly disposed in the body 114 and is configured to longitudinally translate along the central longitudinal axis 120. As shown in FIG. 3A, slider 140 includes an internal portion 142 that slides along a track 144 inside body 114.

Referring now to FIGS. 4-8, a hook 150 extends distally from the internal portion 142 of slider 140 and is configured to slide through the proximal slot 130, through the expander receiver 126, and the distal slot 132 and out the discharge port 122. Hook 150 can be constructed from a biocompatible metal or other rigid material.

The hook 150 comprises an extension member 152 that extends downwardly from a distal end of hook 150. A pushing portion 154 extends distally from the extension member 152 and is configured to push the ring 170 distally from the expander receiver 126 through the discharge port 122. Conversely, a pulling portion 156 extends proximally from the extension member 152 and is configured to pull the ring 170 proximally through the discharge port 122 and into the expander receiver 126. A nub 158 extends laterally from hook 150 and can be used to prevent the ring 170, when folded, from rising above hook 150.

Figure 9:
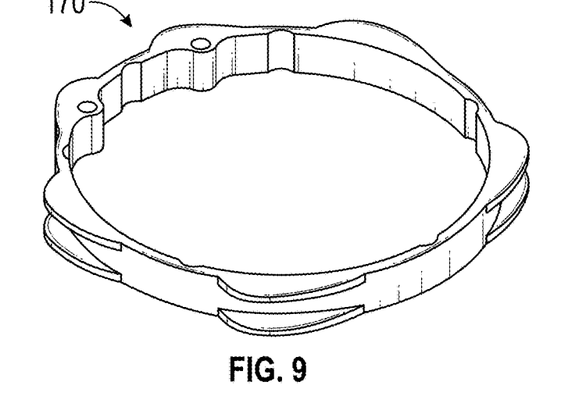
FIG. 9 is a perspective view of an expander ring used with the pupil expander assembly of FIG. 1.
Figure 10:
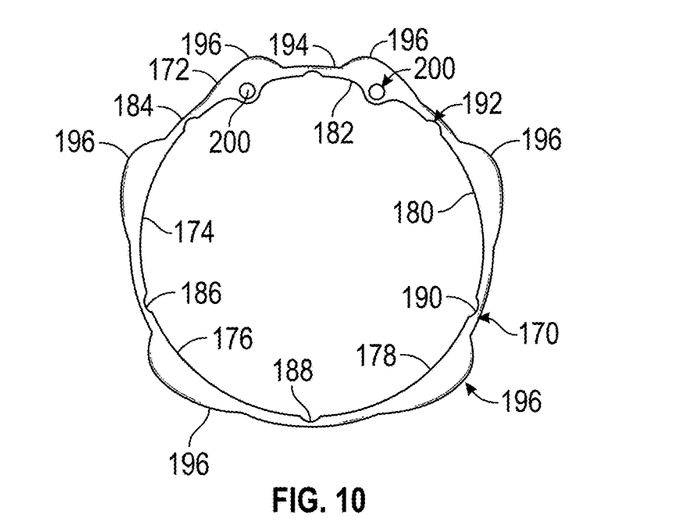
FIG. 10 is a top plan view of the expander ring of FIG. 9.
Figure 11:
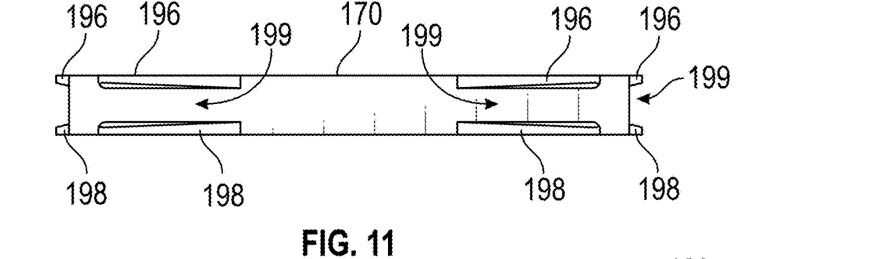
FIG. 11 is a side elevational view of the expander ring of FIG. 9.

Referring to FIGS. 9-11, pupil expander ring 170 is disposed in the expander receiver 126 and is configured to be pushed distally by the hook 150 through the distal slot 130 and the discharge port 122 for delivery to eye 50. The pupil expander ring 170 comprises a ring having a plurality of connected arcuate members 172, 174, 176, 178, 180, 182, which are described, in adjacent order, rotating counter-clockwise from the top left member 172 of FIG. 10: a lateral distal portion 172; a lateral mid portion 174 attached to the lateral distal portion 172; a lateral proximal portion 176 attached to the lateral mid portion 174; a medial proximal portion 178 attached to the lateral proximal portion 176; a medial mid portion 180 attached to the medial proximal portion 178; and a medial distal portion 182 attached to the medial mid portion 180 and to the lateral distal portion 172. A separate living hinge 184, 186, 188, 190, 192, 194 attaches each of the plurality of arcuate members 172, 174, 176, 178, 180, 182 to an adjacent of the plurality of arcuate members 172, 174, 176, 178, 180, 182. Living hinges 184, 186, 188, 190, 192, 194 allow ring 170 to be compressed to fit through distal slot 130 and discharge port 122 for discharge from device 100.

Figure 12A:
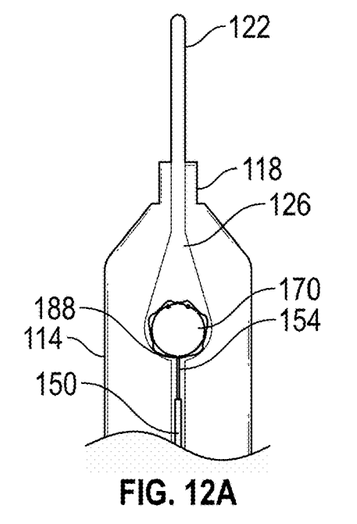
FIG. 12A is a schematic view of a method of engaging the expander ring of FIG. 9 to discharge the ring from the pupil expander assembly of FIG. 1.
Figure 12B:
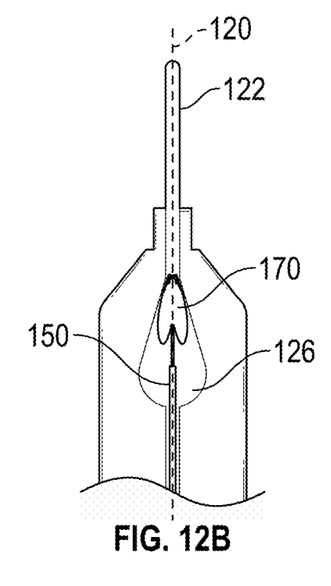
FIG. 12B is a schematic view of a method of advancing the expander ring into the discharge port of the pupil expander assembly of FIG. 1.

As the pupil expander ring 170 is advanced distally through the discharge port 122, the lateral proximal portion 176 and the medial proximal portion 178 are advanced toward a center of the pupil expander ring 170 such that the lateral distal portion 172, the lateral mid portion 174, the medial proximal portion 182, and medial mid portion 180 all collapse inwardly toward the central longitudinal axis 120 to the position shown in FIG. 12B.

Each of the arcuate members 172, 174, 176, 178, 180, 182 further includes an upper lip 196 and a lower lip 198 protruding outwardly therefrom, forming a pocket 199 in between, as shown in FIG. 11. The pocket 199 is sized to allow the sides of the iris 52 to be engaged by the pocket 199 so that the iris 52 is engaged by pupil expander ring 170 and pushed back to revel more of pupil 54. Each of the upper lip 196 and the lower lip 198 has an arcuate profile tapering from larger to smaller in a distal-to-proximal direction. The arcuate profile provides structural integrity to the ring 170, as well as sufficient contact area over the surface of iris 52, and allows uniform peripheral structure when ring is collapsed. Each of the lateral distal portion 172 and the media distal portion 182 has a manipulation hole 200 formed therein. The manipulation holes 200 allow a Sinskey hook, or a dialer (not shown), or other ophthalmic intra-coupler manipulation instrument to adjust or rotate pupil expander ring 170.

In an exemplary embodiment, pupil expander ring 170 can be constructed from Thermoplastic Polyurethane (TPU) or other biocompatible pliable material.

Figure 12C:
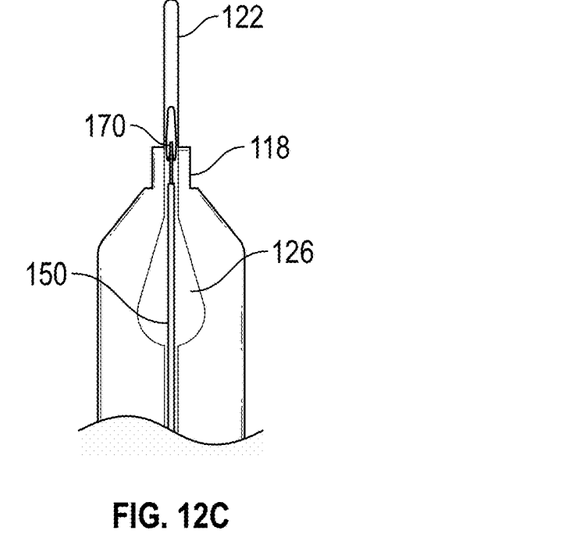
FIG. 12C is a schematic view of a method of advancing the expander ring through the discharge port of the pupil expander assembly of FIG. 1.

To insert pupil expander ring 170 into an eye 50, as shown in FIGS. 12A-12C and 13A-13D, slider 140 is slid distally along body 114, thereby also advancing hook 150 distally. As shown in FIG. 12A, pushing portion 154 of hook engages living hinge 188. The lateral proximal portion 176 and the medial proximal portion 178 are advanced toward a center of the pupil expander ring 170 such that the lateral distal portion 172, the lateral mid portion 174, the medial proximal portion 182, and medial mid portion 180 all collapse inwardly toward the central longitudinal axis 120, as shown in FIG. 12B. As shown in FIG. 12C, pupil expander ring 170 is advanced distally through distal slot 132 of expander receiver 128 and through discharge port 122 for installation into the eye 50.

Figure 13A:
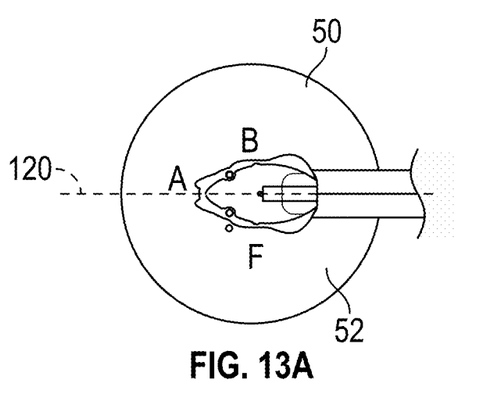
FIG. 13A is a schematic view of the expander ring of FIG. 9 initially engaging the iris of an eye.
Figure 13B:
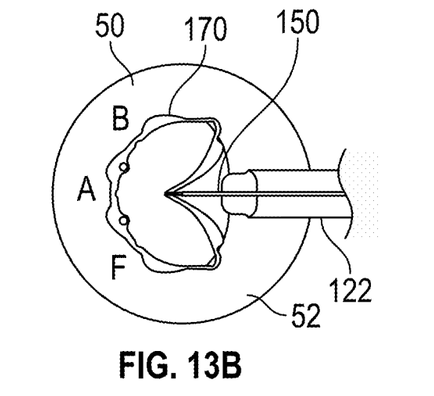
FIG. 13B is a schematic view of the ring of FIG. 13A further engaging the iris.
Figure 13C:
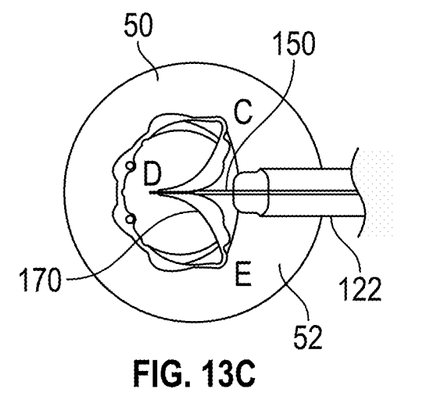
FIG. 13C is a schematic view of the ring of FIG. 13B still further engaging the iris.
Figure 13D:
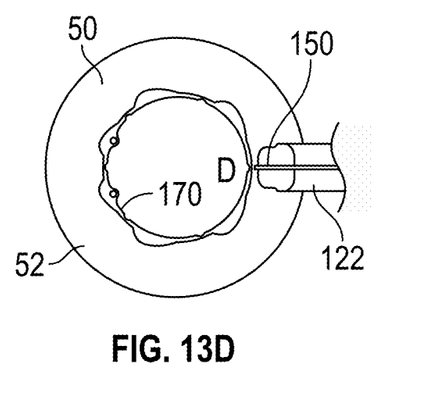
FIG. 13D is a schematic view of the ring of FIG. 13C fully engaging and expanding the iris.

As shown in FIG. 13A, as pupil expander ring 170 exits from discharge port 122, pupil expander ring 170 expands away from central longitudinal axis 120. At this stage, iris 52 begins to be engaged within pocket 199 at points A, B, and F in FIG. 13B, and then to further engage at points C and E in FIG. 13C. After pupil expander ring 170 is fully deployed from device 110, as shown in FIG. 13D, hook 150 is retracted proximally such that pupil expander ring 170 fully engages iris 52, expanding to also engage at point D.

Figure 14A:
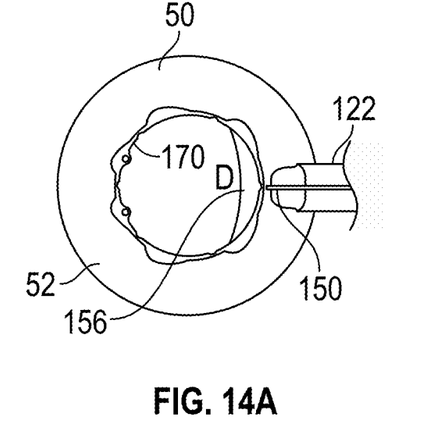
FIG. 14A is a schematic view of the pupil expander assembly of FIG. 5 engaging the expander ring to remove the ring from the iris.
Figure 14B:
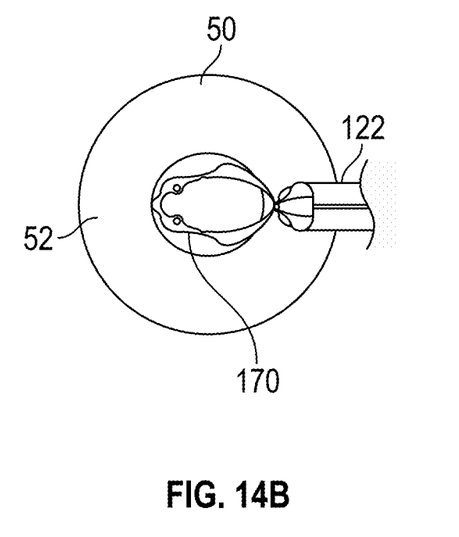
FIG. 14B is a schematic view of the expander ring of FIG. 14A being fully disengaged from the iris.

FIGS. 14A-14B show the removal of expander ring 170 from eye 50. Referring to FIG. 14A, expander ring 170 is disengaged from hook 150 at D by manipulating expander ring 170 with hook 150. Pulling portion 156 engages expander ring 170 and hook 150 is retracted distally into discharge port 122, as shown in FIG. 14B, fully removing expander ring 170 from eye 50.

FIGS. 16-21D provide alternative embodiments of elements of a pupil expander assembly according to the present invention that can be used in any combination as substitutes for similar elements of assembly 100 described above. Corresponding elements described below are comparable to elements described above, with reference numerals 1xx above replaced with reference numerals 2xx below and reference numerals 2xx above are replaced with reference numerals 3xx, where applicable.

Figure 15:
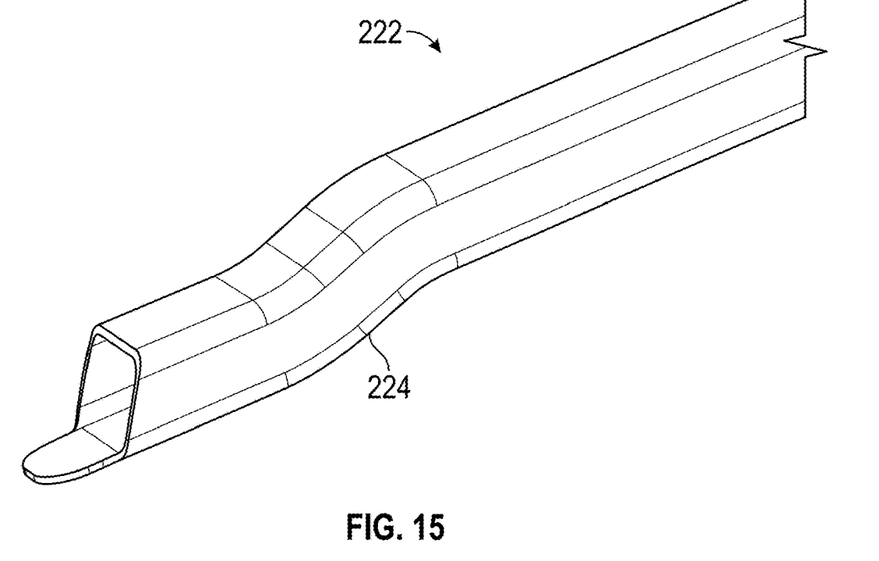
FIG. 15 is a perspective view of an alternative embodiment of a discharge port that extends distally from the distal end portion of the body of the pupil expander assembly.
Figure 16:
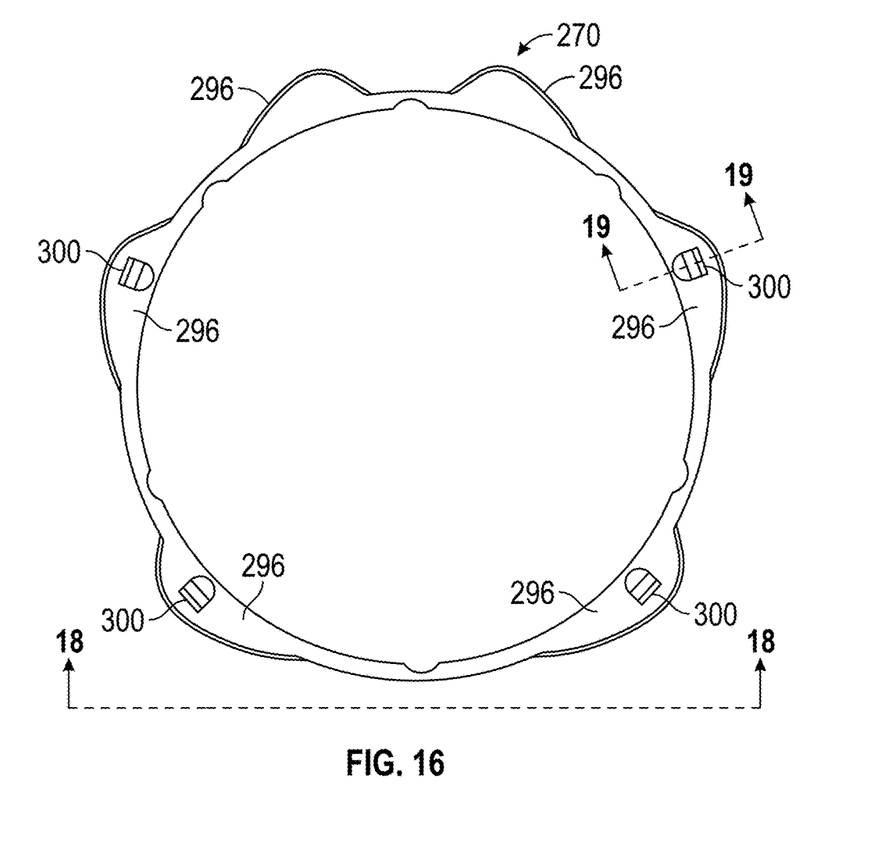
FIG. 16 is a top plan view of an alternative embodiment of an expander ring used in the pupil expander assembly of FIG. 1.
Figure 17:
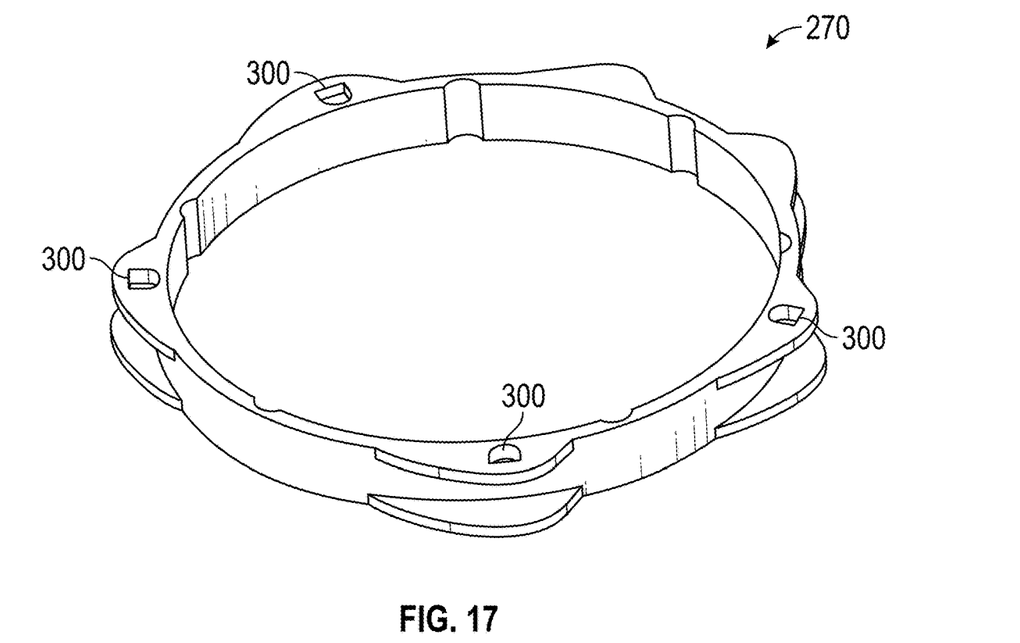
FIG. 17 is a perspective view of the expander ring of FIG. 16.
Figure 18:
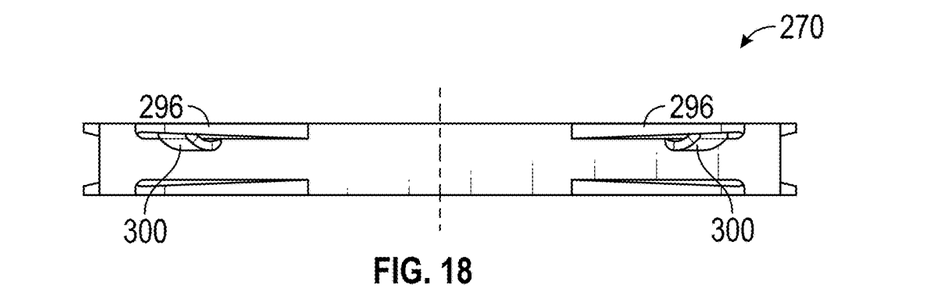
FIG. 18 is a side elevational view of the expander ring of FIG. 16, taken along lines 18-18 of FIG. 16.

FIG. 15 shows an alternative embodiment of a discharge port 222 at the distal end of the assembly. Port 222 incorporates a dogleg 224 toward a distal end of port 222. Dogleg 224 allows the assembly to approach eye 50 at a flatter angle relative to iris 5, providing better access for expander ring 170 to engage iris 52.

Figure 19:
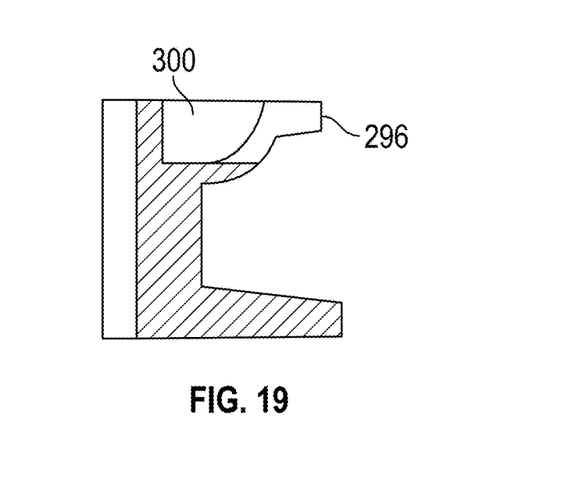
FIG. 19 is a sectional view of a prong engagement portion of the expander ring of FIG. 16, taken along lines 19-19 of FIG. 16.

FIGS. 16-19 show an alternative embodiment of an expander ring 270. Instead of manipulation holes 200 located inside ring 170 as shown in FIG. 10, manipulation holes 300 are provided on the exterior of flanges 296. As shown in FIG. 19, manipulation holes 300 are not through holes, but bottom out to prevent a manipulation device from extending to iris 52 and possible scratching iris 52 as iris 52 is being expanded by ring 270.

Figure 20:
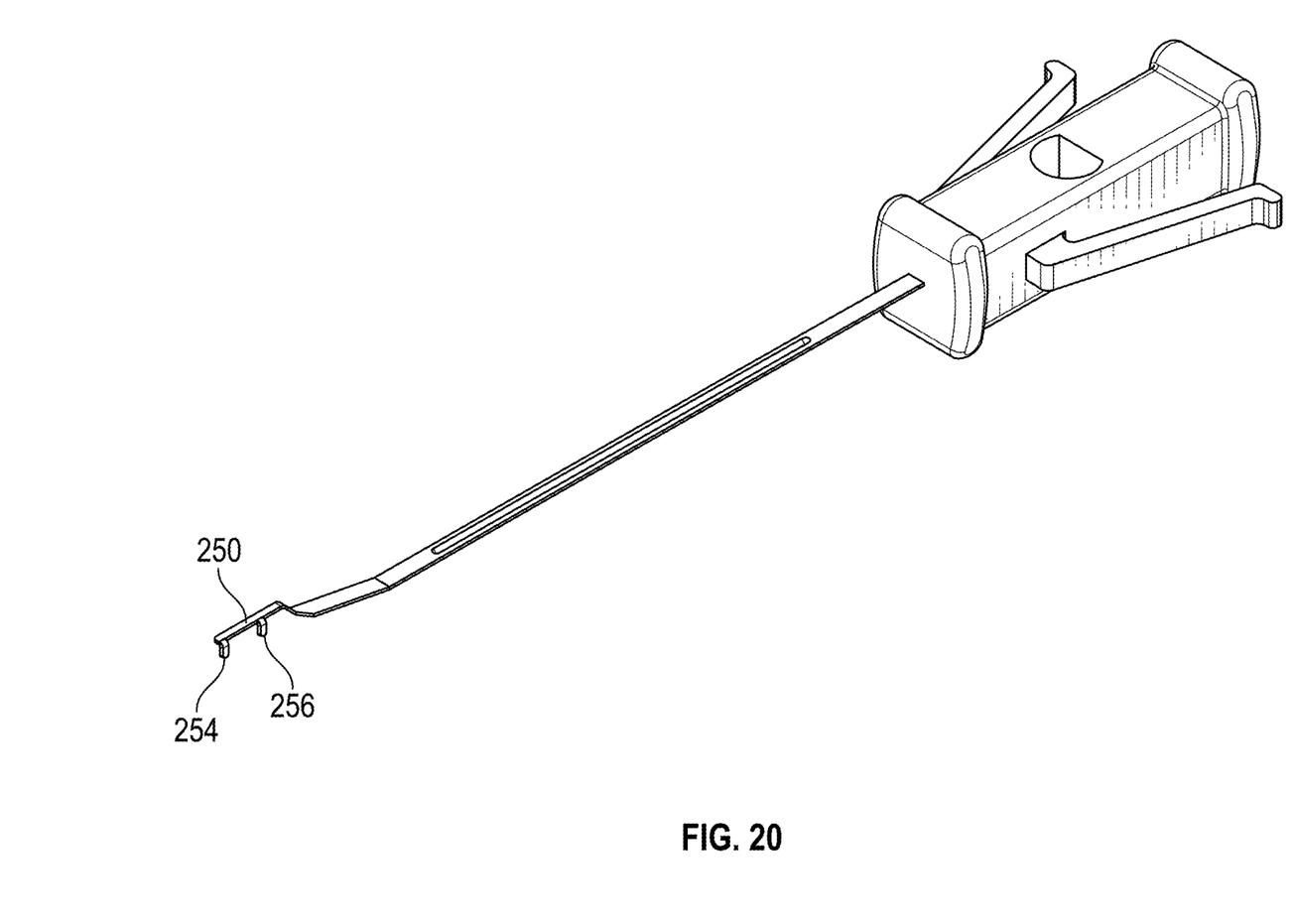
FIG. 20 is a perspective view of an alternative embodiment of a hook assembly used with the pupil expander assembly of FIG. 1.

FIG. 20 shows an alternative embodiment of a hook 250. Hook 250 is used to engage expander ring 170/270 and advance expander ring 170/270 through port 122/222 to iris 52. A distal prong 254 extends outwardly and downwardly from hook 250, and a proximal prong 256 extends parallel to prong 254.

Figure 21A:
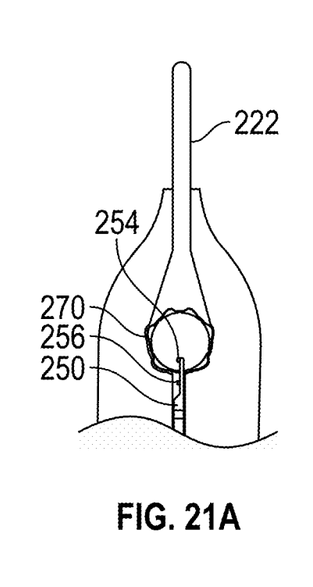
FIG. 21A is a schematic view of the beginning of a method of advancing the expander ring of FIG. 16 with the hook of FIG. 20.
Figure 21B:
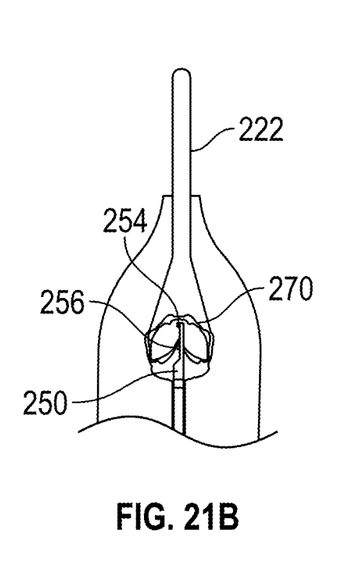
FIG. 21B is a schematic view of the hook of FIG. 20 engaging the expander ring of FIG. 16.
Figure 21C:
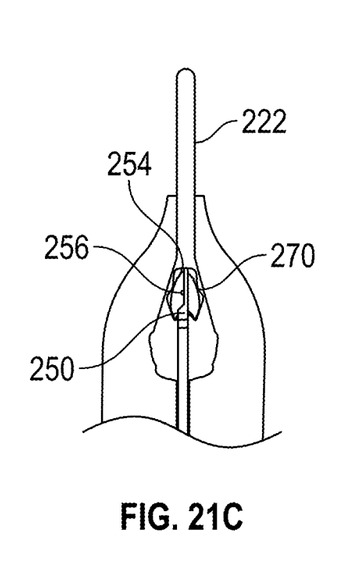
FIG. 21C is a schematic view of the hook of FIG. 20 pushing the expander ring of FIG. 16 into the discharge port.
Figure 21D:
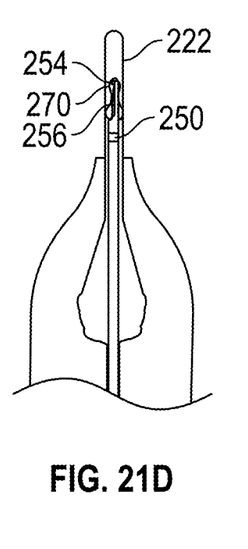
FIG. 21D is a schematic view of the hook of FIG. 20 and the expander ring of FIG. 16 fully advanced into the discharge port.

FIGS. 21A-21D show how hook 250 engages ring 270 (similarly, although not described, hook 250 can engage and advance expander ring 170). In FIG. 21A, prong 254 is inside expander ring 270 and prong 256 is proximal of expander ring 270. Hook 250 is advanced distally to the position shown in FIG. 21B, where prong 256 has engaged expander ring 270 and advanced a proximal end of expander ring 270 distally, toward a distal end of expander ring 270. As shown in FIG. 21C, prong 254 has engaged the distal end of expander ring 270 and advances the distal end of expander ring 270 along with prong 256 advancing proximal end of expander ring 270 distally. This engagement prevents the proximal end of expander ring 270 from "collapsing" against the distal end of expander ring 270, possibly entangling or deforming expander ring 270 with itself. FIG. 21D shows prongs 254, 256 advancing expander ring 270 through tube 222 for placement against iris 250 (not shown in this Figure).

It will be further understood that various changes in the details, materials, and arrangements of the parts which have been described and illustrated in order to explain the nature of this invention may be made by those skilled in the art without departing from the scope of the invention as expressed in the following claims.

We claim:

1. A pupil expander assembly comprising:
   a delivery device comprising:
      a body having a proximal end portion, a distal end portion, and a central longitudinal axis extending between the proximal end portion and the distal end portion;
      a discharge port extending distally from the distal end portion;
      an expander receiver located inside the body in the distal end portion, the expander receiver having a proximal slot and a distal slot, both of the proximal slot and the distal slot extending along the central longitudinal axis, the proximal slot and the distal slot both being in fluid communication with the discharge port;
      a slider slidingly disposed in the body and configured to longitudinally translate along the central longitudinal axis; and
      a hook extending distally from the slider and configured to slide through the proximal slot and the distal slot and out the discharge port;
   a pupil expander disposed in the expander receiver in an expanded condition and configured to be pushed distally by the hook through the distal slot and the discharge port for delivery to an eye; and
   a lens attached to the body and disposed above the expander receiver.

2. The pupil expander assembly according to claim 1, wherein the expander receiver tapers from wider to narrower in a proximal to distal direction.

3. The pupil expander assembly according to claim 1, wherein a wall defining the expander receiver comprises a plurality of detents extending into the expander receiver.

4. The pupil expander assembly according to claim 1, wherein the pupil expander comprises a ring having a plurality of connected arcuate members.

5. The pupil expander assembly according to claim 4, wherein the plurality of arcuate members comprise:
   a lateral distal portion;
   a lateral mid portion attached to the lateral distal portion;
   a lateral proximal portion attached to the lateral mid portion;
   a medial proximal portion attached to the lateral proximal portion;
   a medial mid portion attached to the medial proximal portion; and
   a medial distal portion attached to the medial mid portion and to the lateral distal portion.

6. The pupil expander assembly according to claim 5, further comprising a separate living hinge attaching each of the plurality of arcuate members to an adjacent of the plurality of arcuate members.

7. The pupil expander assembly according to claim 5, wherein each of the lateral distal portion and the medial distal portion has a manipulation hole formed therein.

8. The pupil expander assembly according to claim 5, wherein each of the arcuate members further includes an upper lip and a lower lip protruding outwardly therefrom.

9. The pupil expander assembly according to claim 8, wherein each of the upper lip and the lower lip comprises an arcuate profile tapering from larger to smaller in a distal-to-proximal direction.

10. The pupil expander assembly according to claim 5, wherein as the ring is advanced distally through the discharge port, the lateral proximal portion and the medial proximal portion are advanced toward a center of the ring such that the lateral distal portion, the lateral mid portion, the medial proximal portion, and medial mid portion all collapse inwardly toward the central longitudinal axis.

11. The pupil expander assembly according to claim 1, wherein the hook comprises an extension member extending therefrom, the extension member having a pushing portion extending distally therefrom and configured to push the ring distally from the expander receiver through the discharge port.

12. The pupil expander according to claim 11, wherein the extension member further comprises a pulling portion extending proximally therefrom and configured to pull the ring proximally through the discharge port and into the expander receiver.

13. A pupil expander delivery device comprising:
   a body having a proximal end portion, a distal end portion, and a central longitudinal axis extending between the proximal end portion and the distal end portion;
   a discharge port extending distally from the distal end portion;
   an expander receiver located inside the body in the distal end portion, the expander receiver having a proximal slot and a distal slot, and is sized to store a pupil expander in an expanded condition, both of the proximal slot and the distal slot extending along the central longitudinal axis, the proximal slot and the distal slot both being in fluid communication with the discharge port;
   a slider slidingly disposed in the body and configured to longitudinally translate along the central longitudinal axis;
   a hook extending distally from the slider and configured to slide through the proximal slot and the distal slot and out the discharge port; and
   a lens attached to the body and disposed above the expander receiver.

14. The pupil expander delivery device according to claim 13, wherein the expander receiver tapers from wider to narrower in a proximal to distal direction.

15. The pupil expander delivery device according to claim 13, wherein a wall defining the expander receiver comprises a plurality of detents extending into the expander receiver.

16. The pupil expander delivery device according to claim 13, wherein the hook comprises an extension member extending therefrom, the extension member having a pushing portion extending distally therefrom and configured to push the ring distally from the expander receiver through the discharge port.

17. The pupil expander delivery device according to claim 16, wherein the extension member further comprises a pulling portion extending proximally therefrom and configured to pull the ring proximally through the discharge port and into the expander receiver.

18. The pupil expander delivery device according to claim 13, wherein the hook is configured to be retracted distal of the expander receiver.

* * * * *